United States Patent [19]

Castaldi et al.

[11] Patent Number: 5,004,832
[45] Date of Patent: Apr. 2, 1991

[54] PREPARING ALPHA-ARYLALKANOIC ACIDS

[75] Inventors: Graziano Castaldi, Briona; Claudio Giordano, Vicenza, both of Italy

[73] Assignee: Zambon S.p.A., Vicenza, Italy

[21] Appl. No.: 306,755

[22] Filed: Feb. 6, 1989

Related U.S. Application Data

[62] Division of Ser. No. 891,348, Jul. 31, 1986, Pat. No. 4,824,970.

[30] Foreign Application Priority Data

Jul. 31, 1985 [IT] Italy ............................ 21803 A/85

[51] Int. Cl.$^5$ .................. C07C 63/36; C07C 63/04; C07D 333/22
[52] U.S. Cl. .................. 562/490; 562/465; 562/466; 562/471; 562/472; 562/493; 568/319; 568/591; 568/592; 549/60; 549/70; 549/296
[58] Field of Search ............ 562/490, 471, 472, 493, 562/465, 466; 549/70

[56] References Cited

U.S. PATENT DOCUMENTS

| 4,579,968 | 4/1986 | Castaldi et al. | 562/490 |
|---|---|---|---|
| 4,582,930 | 4/1986 | Castaldi et al. | 562/490 |

OTHER PUBLICATIONS

Fieser et al., *Advanced Organic Chemistry*, p. 574 (1961).

*Primary Examiner*—Glennon H. Hollrah
*Assistant Examiner*—Amelia A. Owens
*Attorney, Agent, or Firm*—Cushman, Darby & Cushman

[57] ABSTRACT

Compounds are described of formula

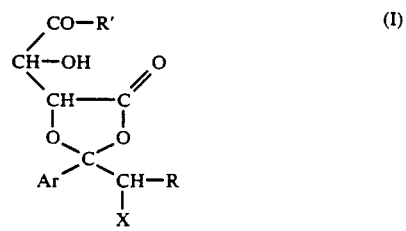

(I)

in which:

Ar represents an aryl, possibly substituted;

R represents a $C_1$-$C_4$ alkyl;

R' represents a hydroxyl, an alkoxy, an amino group possibly mono or di-alkyl substituted, or an O$^-$M$^+$ group where M$^+$ represents the cation of an alkaline metal;

X represents a hydrogen, chlorine, bromine or iodine atom, a hydroxyl, or an acyloxy, alkylsulphonyloxy or arylsulphonyloxy group.

The compounds of formula I can be easily transformed into alpha-arylkanoic acids of formula

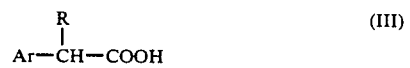

(III)

in which Ar and R have the aforesaid meanings.

2 Claims, No Drawings

PREPARING ALPHA-ARYLALKANOIC ACIDS

This is a division of application Ser. No. 06/891,348, filed July 31, 1986 now U.S. Pat. No. 4,824,970.

This invention relates to new intermediates for the preparation of carboxylic acids, and more particularly relates to new compounds having a lactone structure and their use in the synthesis of alpha-arylalkanoic acids.

Numerous alpha-arylalkanoic acids are known for their pharmaceutical properties (anti-inflammatory, analgesic).

These include 2-(4-isobutylphenyl)-propionic acid known as Ibuprofen, 2-(3-phenoxyphenyl)-propionic acid known as Fenoprofen, 2-(2-fluoro-4-diphenylyl)-propionic acid known as Flurbiprofuen, 2[4-(2-thienylcarbonyl)-phenyl]-propionic acid known as Suprofen, 2-(2-methoxy-2-naphthyl)-propionic acid the (S) isomer of which is known as Naproxen, and others.

A further group of alpha-arylalkanoic acids are useful as intermediates in the preparation of pyrethrum insecticides. These include 2-(4-chlorophenyl)-3-methyl-butyric acid and 2-(4-difluoromethoxy-phenyl)-3-methyl-butyric acid.

The present invention has as its subject the new compounds of formula I given hereinafter which have proved to be very useful and particularly versatile intermediates in the synthesis of alpha-arylalkanoic acids.

As far as we know, neither the compounds of formula I nor the use of lactone derivatives in the synthesis of alpha-arylalkanoic acids has ever been previously described.

The compounds according to the present invention fall within the following general formula:

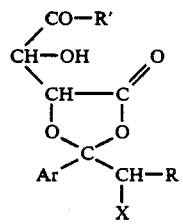

in which:
Ar represents an aryl, possibly substituted;
R represents a $C_1$-$C_4$ alkyl;
R' represents a hydroxyl, an alkoxy, an amino group possibly mono or di-alkyl substituted, or an O—$N^+$ group where $N^+$ represents the cation of an alkaline metal;
X represents a hydrogen, chlorine, bromine or iodine atom, a hydroxyl, or an acyloxy, alkylsulphonyloxy or arylsulphonyloxy group.

With regard to the meanings of the aforesaid substituents, the term "aryl, possibly substituted" means in particular the aryl group of those alpha-arylalkanoic acids useful in the pharmaceutical or agricultural field such as 4-isobutyl-phenyl, 3-phenoxy-phenyl, 2-fluoro-4-diphenylyl, 4-(2-thienylcarbonyl)phenyl, 6-methoxy-2-naphthyl, 5-bromo-6-methoxy-2-naphthyl, 6-hydroxy-2-naphthyl, 4-chloro-phenyl, 4-difluoromethoxy-phenyl etc.

The specific meanings of R for the purpose of preparing arylalkanoic acids useful in the pharmaceutical or agricultural field include methyl and isopropyl.

The group CO—R' represents a carboxyl or one of its functional derivatives (ester, amide, alkaline carboxylate). The possibility of interconversion between these groups by common chemical reactions enables certain chemical-physical parameters of the compounds of formula I to be varied, and in particular enables its solubility to be varied between wide limits in the particular solvent chosen in the preparation of alpha-arylalkanoic acids in accordance with the procedures specified hereinafter.

The choice of the group X (where X is other than hydrogen) also depends on the type of procedure chosen for preparing the alpha-arylalkanoic acids.

The compounds of formula I are prepared by a rearrangement reaction on the ketal derivatives of formula II catalysed by a strong acid or by an ammonium salt of a strong acid.

As far as we know, the rearrangement of a ketal to lactone has no precedent in the literature.

The ketals useful for the preparation of compounds of formula I, in accordance with the experimental conditions specified hereinafter, fall within the following general formula:

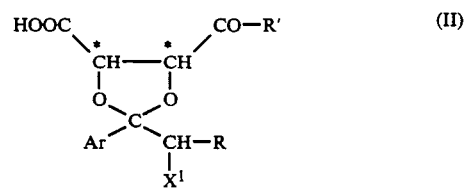

in which
Ar, R and R' have the meanings given for general formula I, and
$X_1$ represents a hydrogen, chlorine, bromine or iodine atom or a hydroxyl;
the carbon atoms indicated by an asterisk both have R or S configuration.

The compounds of formula II, their preparation and their use in the synthesis of alpha-arylalkanoic acids are described in the copending Italian patent applications Nos. 7204 A/84, 7205 A/84 and 7207 A/84 in the name of the present applicant.

From the compounds of formula II, the compounds of formula I are obtained in which X has the same meanings as $X_1$.

Finally, if required, the compounds of formula I in which X represents an acyloxy, alkylsulphonyloxy or arylsulphonyloxy group are prepared from the compounds of formula I in which X is a hydroxyl by conventional methods, for example by reaction with the appropriate acyl halide.

Ignoring any other centers of asymmetry which may be present in the substituents Ar, R and R', the compounds of formula I have four centers of asymmetry which in the following formula are indicated by the letters a, b, c and d.

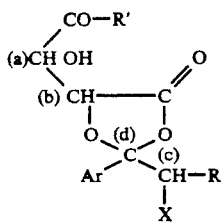

The configuration of the centers of asymmetry a and b is determined by the configuration of the carbon atoms indicated by an asterisk in formula II.

Thus the centers of asymmetry a and b both have R or S configuration.

The result is that the compounds of formula I exist in the form of four diastereoisomers.

Considering for example the case in which the centers of asymmetry a and b both have R configuration, the four diastereoisomers will have the following configurations with reference to the centers of asymmetry a, b, c and d in the order given: RRRR, RRES, RRSR and RRSS.

We have observed that when the center of asymmetry c has S configuration in the compounds of formula I, the alpha-arylalkanoic acids obtained by the procedures specified hereinafter have S configuration independently of the configurations of the other three centers of asymmetry.

This fact is particularly important in that most practical interest is generally associated with the S enantiomer of alpha-arylalkanoic acids.

It is also important to note that when the center of asymmetry c has R configuration in the compounds of formula I, the alpha-arylalkanoic acids obtained have R configuration and that, in any event, the relative abundance of a particular enantiomer in the alpha-arylalkanoic acids obtained from compounds of formula I reflects the diastereoisomeric ratio of the compounds of formula I with reference to the center of asymmetry c.

As stated heretofore, compounds of formula I are prepared by treating a compound of formula II with a strong acid or with an ammonium salt.

The reaction is conducted by adding the acid or the ammonium salt to a solution of compound II in an inert solvent.

Alternatively, the ammonium salt can be generated within the reaction environment by adding a tertiary amine.

Particularly suitable acids are hydrochloric, hydrobromic, sulphuric, methanesulphonic, trifluoroacetic, trifluoromethanesulphonic, fluorosulphonic and hexafluorocantiomonic acids.

The ammonium salt, whether generated in situ or prepared separately, include salts of strong acids with tertiary amines such as pyridine bromide and triethylammonium bromide.

The inert solvent can be chosen from chlorinated hydrocarbons, aromatic hydrocarbons or cyclic ethers, for example carbon tetrachloride, 1,1-dichloroethane, benzene, toluene and tetrahydrofuran.

The configuration of the center of asymmetry c in the compounds of formula I obtained in this manner reflects the configuration of the carbon atom carrying the substituent X in the compounds of formula II (where X is other than H).

This means that the ratio of the sum of the two diastereoisomers of the compounds of formula I which have their centre of asymmetry c in R configuration to the sum of the two diastereoisomers which have their center of asymmetry c in S configuration reflects the ratio of the epimers (R/S) in the compounds of formula II, with reference to the carbon atom carrying the substituent $X_1$.

In other words, starting from an individual epimer of the compound of formula II, for example the S epimer with reference to the carbon atom carrying the substituent $X_1$, only the two diastereoisomers of the compound of formula I having their center of asymmetry c in S configuration are obtained.

It has also been surprisingly found that the compounds of formula I can be prepared from the compounds of formula II by an alternative procedure which has certain practical advantages in that it enables the compounds of formula I to be directly obtained enriched with diastereoisomers having a determined configuration at the center of asymmetry c.

As stated heretofore, it is the configuration of the centre of asymmetry c which determines the relative abundance of the two enantiomers in the alpha-arylalkanoic acids obtained from the compounds of formula I.

This alternative procedure consists of simultaneously halogenating compounds II in which X=H and transforming them into compounds I.

The reaction is conducted under conditions analogous to those described heretofore, is in the presence of an ammonium salt and also in the presence of a suitable halogenating agent. These include bromine, quternary ammonium perhalides and iodine chloride.

Compounds of formula I in which X represents a bromine, chlorine or iodine atom are thus obtained.

Surprisingly however, the reaction is diastereoselective in that the four diastereoisomers of the compounds of formula I are never obtained in equimolar quantities. In particular, if for example the carbon atoms indicated by an asterisk in formula II both have R configuration, the sum of the diastereoisomers having their center of asymmetry c in S configuration will prevail in the products of formula I. Starting however from compounds of formula II in which the carbon atoms indicated by an asterisk both have S configuration, the sum of the diastereoisomers having their center of asymmetry c in R configuration will prevail in the products of formula I.

It is important to note that the conversion yields are very high and practically quantitative.

A further interesting aspect of the compounds of formula I is that the prevailing diastereoisomer can be obtained in pure form by fractional crystallisation.

In addition to the compounds of formula I and their preparation, a further subject of the present invention is the use of the compounds of formula I in the preparation of alpha-arylalkanoic acids of formula

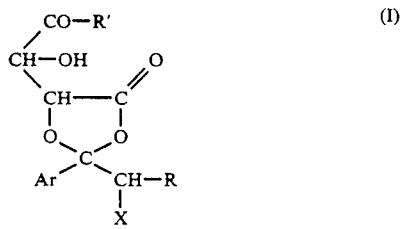

(in which Ar and R have the meanings given for formula I) or of their immediate precursors such as the corresponding salts or esters.

The intrinsic properties of the lactone structure of the compounds of formula I makes them very versatile thus enabling the alpha-arylalkanoic acids to be prepared by various alternative methods.

Of most immediate interest is the direct transformation of the compound of formula I into the acid III or one of its precursors. The compounds of formula I in which $X=Cl, Br, I, O\text{-acyl}, O—SO_2\text{-alkyl}$ and $O—SO_2\text{-aryl}$ can be transformed by simply heating in a protic polar solvent or in an aprotic dipolar solvent in the presence of a substance having a high dielectric constant, in a neutral or slightly alkaline environment. Depending on the reaction solvent, the product will either be an alkaline salt or an ester of the corresponding acid of formula III. This latter is easily obtained in free form by acidification or by hydrolysis of the immediate precursor ester respectively.

The compounds of formula I in which $X=Cl, Br, I$ can also be transformed directly into the corresponding alpha-arylalkanoic acids or their precursors by reacting the compound of formula I in an inert solvent with a metal catalyst pertaining to the soft or borderline group of Lewis acids (J. March, "Advanced Organic Chemistry", page 229, 3rd Edition, John Wiley & Son). Specific examples of these compounds are organic or inorganic salts of the following cations: $Cu^+, Ag^+, Cu^{++}, Pd^{++}, Pt^{++}, Hg^{++}, Fe^{++}, Co^{++}, Zn^{++}, Sn^{++}, Sb^{+++}$ and $Bi^{+++}$.

The reaction provides the compounds of formula III in the form of esters.

There is also great practical interest in the basic hydrolysis of compounds of formula I in which $X=Cl, Br, I$ to give ketones of formula

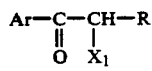

(in which $X_1=Cl, Br, I$).

The ketones of formula IV are known compounds, and their transformation into the corresponding acids of formula III by a rearrangement reaction is also known. Of particular importance is the fact that, as heretofore stated, the compounds of formula I can be easily prepared stereoselectively to obtain a mixture of diastereoisomers in which those having their center of asymmetry c of S configuration or, if required, of R configuration strongly prevail.

Their hydrolysis leads to optically active ketones of formula IV. The carbon atom carrying the substituent $X_1$ has the same configuration as the center of asymmetry c in the starting lactones.

A compendium of the known synthesis methods for preparing alpha-arylalkanoic acids from ketones of formula IV, including optically active ketones, by way of the formation of the corresponding ketals derived from them, is given in the description of European patent application No. 81993 in the name of Syntex, in which the invention particularly relates to the synthesis of optically active ketones IV by reacting an aryl-magnesium halide with an optically active acyl halide.

A more convenient synthesis method for the preparation of optically active alpha-arylalkanoic acids from optically active ketones of formula IV is to react these latter in a protic medium with a metal catalyst pertaining to the soft or borderline group of Lewis acids.

Of the alpha-arylalkanoic acids of pharmaceutical interest, 2-(6-methoxy-2-naphthyl)-propionic acid is of particular importance is that its $S(+)$ isomer is used as an anti-inflammatory and analgesic under the common name of Naproxen.

In order to avoid the costly stage of separating the $S(+)$ isomer from the raceme mixture, an enantioselective synthesis method which leads to the $S(+)$ isomer or at least to a mixture strongly enriched with the $S(+)$ isomer is desirable.

One aspect of the present invention is the preparation of Naproxen by the transformation, using the aforesaid methods, of the specific compounds of formula I-A

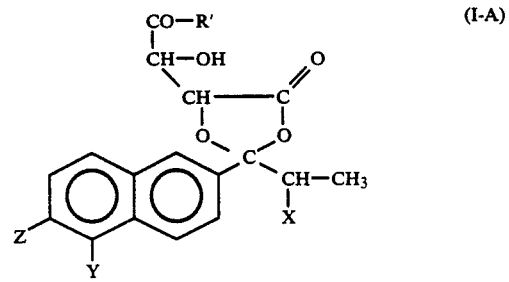

in which R' and X have the meanings given for formula I, Y represents a hydrogen or bromine atom, and Z represents a hydroxyl, methoxy or $O—M^+$ group where $M^+$ is the cation of an alkaline salt.

The compounds of formula I-A are obtained from the suitable compound of formula II by the aforesaid procedure. Because in this case the main purpose is to obtain the compound I-A rich in the stereoisomer or stereoisomers which lead to Naproxen, the preferred procedure is that comprising stereoselective halogenation of the compound II in which $X_1=H$, or alternatively the compound II rich in the required epimer is treated with acids.

As heretofore stated, for the preparation of Naproxen, the center of asymmetry of the compound I-A carrying the substituent X must be mainly or totally of S configuration.

This is obtainable by halogenating the compound II ($X=H$) in which the carbon atoms indicated by an asterisk have both R configuration, or by acid treatment of the compound II in which the carbon atom carrying the substituent $X_1$ is mainly or totally of S configuration.

If the compound II ($X=H$) is halogenated with bromine, the naphthalenic nucleus can also undergo bromination to thus form compounds I-A in which $Y=Br$.

The bromine atom bonded to position 5 of the naphthalenic nucleus is than easily removed, either at the level of the compound I-A or at the level of the arylalkanoic acid, by hydrogenolysis in accordance with conventional methods.

Naproxan is prepared from compounds of formula I by the methods described heretofore in relation to the transformation of compounds of formula I into the corresponding alpha-arylalkanoic acids. Again in this case, basic hydrolysis of the compound I-A in which $X=Cl, Br$ or $I$ leads to the corresponding optically active naphthyl-alpha-haloalkyl-ketone, which is a useful intermediate in the preparation of Naproxen by the aforesaid procedures.

The following examples are given for the purpose of better illustrating the invention, but without limiting it.

EXAMPLE 1

Preparation of 2-(1-bromoethyl)-2-(5-bromo-7-methoxy-2-naphthyl)-5(R)-[(1(R)-hydroxy)-carboxymethyl]-1,3-dioxolan-4-one(1-[(2-(1-bromoethyl)-2-(5-bromo-6-methoxy-2-naphthyl)-1,3-dioxolan-4-one-5(R)-yl]-1(R)-hydroxacetic acid.

A mixture of diastereosimers of 2-(1-bromoethyl)-2-(5-bromo-6-methoxy-2-naphthyl)-4(R),5)(R)-dicarboxy-1,3-dioxolane (1) of RRS:RRR ratio=94:6 (0.504 g; 1 mmole), methanesulphonic acid (0.064 ml; 1 mmole) and 1,2-dichloroethane (3.5 ml) is kept at 40° C. under agitation and under argon for 4.5 hours. The reaction mixture is then dripped into an aqueous 10% sodium bicarbonate solution and extracted with ethyl ether. The aqueous phase is then acidified to pH 1 with concentrated hydrochloric acid and extracted with ethyl ether. The pooled organic phases are washed with water and dried with sodium sulphate. Evaporating the solvent under vacuum leaves the required product (2) which is purified by chromatography in a silica gel column (yield 80%).

The product (II) consists of four diastereoisomers indicated herein as 2a, b, c and d.

I.R. (Nujol): stretching OH: 3550 cm$^-$, 3300 cm$^{-1}$, stretching C=O; 1815 cm$^{-1}$, 1740 cm$^{-1}$,

EXAMPLE 2

Preparation of methyl ester of 1-[2-(1-bromoethyl)-2-(5-bromo-6-methoxy-2-naphthyl)-1,3-dioxolan-4-one-5-(R)-yl)-1(R)-hydroxyacetic acid.

A solution of compound (2) (see Example 1) (100 mg) and methanesulphonic acid (20 mg) in methanol (10 ml) is maintained at reflux temperature for 2 hours. It is cooled to ambient temperature and diluted with dichloromethane (20 ml). It is washed with water and with an aqueous 2% sodium bicarbonate solution, and dried with sodium sulphate. Evaporating the solvent under vacuum leaves the four diastereoisomers of the required product (3) with a yield of 95%.

I.R. (Nujol): stretching OH: 3550 cm$^{-1}$, stretching C=O; 1815 cm$^{-1}$, 1750 cm$^{-1}$.

| Elementary analysis: | C | H | Br |
|---|---|---|---|
| calculated (%) | 44.04 | 3.69 | 30.84 |
| found (%) | 44.00 | 3.72 | 30.91 |

HPLC analysis of the mixture (3) shows the presence of four peaks of which the relative compounds, based on the chromatographic retention time, are indicated as 3a, b, c and d, and correspond to the methyl ester of compounds 2a, b, c and d (see Example 1).

| | Retention time | Relative percentage |
|---|---|---|
| 3a | 13.49 | 3 |
| 3b | 13.89 | 61 |
| 3c | 14.89 | 3 |
| 3d | 15.50 | 33 |

HPLC analysis conditions: Column RP8, spheres 5μ, 1=250 mm. Eluent: methanol 58.5, water 41.5%. Throughput: 1.7 ml/min. Temperature: 40° C.

EXAMPLE 3

Preparation of 1-[2-(1-bromoethyl)-2-(5-bromo-6-methoxy-2-naphthyl)-1,3-dioxolan-4-one-5(R)-yl]-1(R)-hydroxyacetic acid (2)

Bromine (3.2 g; 20 mmoles) is added at 15° C. over 5 minutes to a mixture of 2-ethyl-2-(6-methoxy-2-naphthyl)-4(R),5(R)-dicarboxy-1,3-dioxolane (3.46 g; 10 mmoles), pyridine (0.356 g; 0.362 ml; 4.5 mmoles) and 1,2-dichloroethane (35 ml). The reaction mixture is kept at 15° C. for 3 hours and is then dripped into a 10% sodium bicarbonate solution (150 ml) and extracted with ethyl ether (3×50 ml). The aqueous phase is then acidified to pH 1 with concentrated HCl and extracted with ethyl ether (3×50 ml). The pooled organic phases are washed with water and dried with sodium sulphate. Evaporating the solvent under vacuum leaves the required product (2) (4.73 g; 9.4 mmoles; yield 94%).

HPLC analysis of a sample esterified with diazomethane (conducted in accordance with Example 2) shows that the product consists of the four diastereoisomers 3a, b, c, d in the ratio of 13:65:5:17.

EXAMPLE 4

The mixture of stereoisomers of compound 3 (methyl ester) obtained as described in Example 2 is successively crystallised from methanol to give the pure isomer 3b (HPLC purity exceeding 98%).

$^1$H-NMR (200 MHz, CDCl$_3$-TMS) delta (ppm): 1.32 (d, J=6.8 Hz); 2.62 (d, 1H, J=7.1 Hz): 3.69 (s, 3H); 4.04 (s, 3H); 4.52 (dd, 1H, J$_{CH-CH}$=1.6 Hz, J$_{CH-CH}$=7.1 Hz); 4.60 (q, 1H, J=6.8 Hz); 5.16 (d, 1H, J=1.6 Hz); 7.2-8.3 (aromatic protons 5H).

I.R. (Nujol): stretching OH: 3540 cm$^{-1}$. stretching C=O: 1815 cm$^{-1}$, 1750 cm$^{-1}$.

EXAMPLE 5

Preparation of S(+)-2-(6-methoxy-2-naphthyl)-propionic acid (Naproxen)

A sample of 1-[2-(1-bromoethyl)-2-(5-bromo-6-methoxy-2naphthyl)-1,3-dioxolan-4-one-5(R)-yl]-1(R)-hydroxyacetic acid (0.486 g; 0.965 mmoles) (of which the methyl ester when analysed by HPLC shows the following isomeric composition 3a:3b:3c:3d=15:80.5:0:4.5) is added to a solution of silver trifluoromethanesulphonate (0.37 g; 1.45 mmoles) in methanol (2.5 ml). The reaction mixture is kept at reflux temperature under agitation in darkness for 22 hours. The mixture is then cooled to ambient temperature, diluted with dichloromethane (20 ml), filtered and washed with water. The organic phase is dried with sodium sulphate and the solvent evaporated under vacuum. The residue thus obtained is chromatographed (silica gel, eluent dichloromethane:hexane=1:1) to give the methyl ester of 2-(5-bromo-6-methoxy-2-naphthyl)-propionic acid (0.115 g; 0.356 mmoles; yield 37%).

M.P. 94°-95° C. [α]$_D^{20}$=+32.75° (C=0.5, chloroform).

$^1$H-NMR analysis (300 MHz) conducted with the aid of an optically active shift reagent (tris-[3-heptafluoropropylhydroxymethylene)]-camphorate, Europium III derivative) shows a S(+):R(−) enantiomer ratio of 82:18.

Acid hydrolysis of the compound followed by hydrogenolysis of the bromine atom in position 5 conducted with hydrazine in the presence of 5% palladium on carbon leads to 2-(6-methoxy-2-naphthyl)-propionic acid with the same enantiomer ratio (S:R=82:18).

EXAMPLE 6

Preparation of 2-bromo-1-(5-bromo-6-methoxy-2-naphthyl)propan-1-one.

A solution of sodium hydroxide (0.48 g:12 mmoles) in water (10 ml) is added dropwire at 15° C. to a mixture of diastereoisomers of the 1-[2-(1-bromoethyl)-2-(5-bromo-6-methoxy-2-naphthyl-1,3-dioxolan-4-one-5(R)-yl]1(R)-hydroxyacetic acid (2a:b:c:d=16:50:8:26) (5.04 g; 10 mmoles) and methanol (45 ml). The reaction mixture is kept at 15° C. for 3.5 hours and is then extracted with dichloromethane (3×50 ml). The pooled organic extracts are washed with water and dried with sodium sulphate.

Evaporating the solvent under vacuum leaves 2-bromo-1-(5-bromo-6-methoxy-2-naphthyl)-propan-1-one (4) (2.98 g; 8 m moles; yield 80%).

M.P. 165°-167° C. $[\alpha]_D^{20} = +65.17°$ (C=0.5, chloroform).

$^1$H-NMR analysis (200 MHz) conducted with the aid of an optically active shift reagent (tris-[3-(heptafluoropropylhydroxymethylene)]-camphorate, Europium III derivative) in CDCl$_3$, shows a S(+):R(−) ratio of 70:30.

EXAMPLE 7

Preparation of optically pure S(+)-2-bromo-1-(5-bromo-6-methoxy-2-naphthyl)-propan-1-one Starting with the compound 2-(S)-(1-bromoethyl)-2-(5-bromo-6-methoxy-2-naphthyl)-4(R),5(R)-dicarboxy-1,3-dioxolane and operating in accordance with the procedure described in Example 1, the compound 2-(1-bromoethyl)-2-(5-bromo-6-methoxy-2-naphthyl)-5(R)-hydroxy-6(R)-carboxy-1,3-dioxan-4-one (2) is obtained with a yield of 60%, its HPLC analysis conducted on a sample esterified with diazomethane showing the presence only at the diastereoisomers 3b and 3d in the ratio of 69:31.

The lactone 2 is then hydrolysed by the procedure described in Example 6.

The required compound is obtained with a yield of 90%.

M.P. 168°-169° C. $[\alpha]_D^{20} = +162.2°$ (C=0.5, chloroform).

$^1$H-HMR analysis (200 MHz) conducted with the aid of an optically active shift reagent (tris-[3-(heptafluoropropylhydroxymethylene)]-camphorate, Europium III derivative) in CDCl$_3$, shows the presence only of the S(+) isomer.

EXAMPLE 8

Preparation of S(+)-2(6-methoxy-2-naphthyl)-propionic acid (Naproxen)

S(+)-2-bromo-1-(6-methoxy-2-naphthyl)-propan-1-one (0.568 g; 2 mmoles) is added under agitation at 15° C. to a solution obtained by dissolving silver carbonate (0.331 g; 1.2 mmoles) in BF$_3$·2CH$_3$OH (2 ml).

The reaction mixture is kept at 15° C. for 20 hours, and then filtered.

The filtrate is diluted with dichloromethane, washed with water and dried with sodium sulphate.

Evaporating the solvent under vacuum leaves a residue which after purification in a silica gel column (eluent dichloromethane: hexane=3:7) gives the optically pure methyl ester of S(+)-2-(6-methoxy-2-naphthyl)-propionic acid (0,390 g; 1.6 mmoles; yield 80%).

M.P. 88° C. $[\alpha]_D^{20} = +79.4°$ (C=1, chloroform)

$^1$H-NMR analysis (200 MHz) conducted with the aid of an optically active shift reagent as described in Example 5 shows the presence only of the enantiomer.

Acid hydrolysis of the ester thus obtained leads to optically pure S(+)-2-(6-methoxy-2-naphtyl)-propionic acid.

EXAMPLE 9

The four diastereomers 3a, b, c, d, obtained as described in the example 2, were separated by column chromatography (silica gel 230–400 mesh, eluent hexane:diethylether=7.3).

Diastereomer 3a

M.p.=141° C. I.R. (chloroform) cm$^{-1}$: 1815, 1755 (C=O). $^1$H-NMR(300MHz), CDCl$_3$-TMS)δ(ppm): 1.55(d, 3H, J=7Hz): 2.29(d,1H, J=8.4Hz); 3.88(s, 3H); 4.06(s, 3H); 4.49(dd, 1H, J=8.4Hz, J=1.46Hz); 4.58(Abq, 1H, J=6.6Hz, Δν=11.8Hz); 5.13(d,1H), J=1.46Hz). 7.26–8.30(5H, aromatic protons). Mass (isobutane) m/e (%): 521(20.61); 519(41.10); 517(20.98).

Diastereomer 3b

M.p.=193° C. I.R. (chloroform) cm$^{-1}$: 1815, 1755 (C=O). $^1$H-NMR(300 MHz, CDCl$_3$-TMS)δ(ppm): 1.53(d, 3H, J=7 Hz); 2,63(d, 1H), J=7.33 Hz); 3.97(s, 3H); 4.05(s, 3H); 4.56(dd, 1H, J=7.33 Hz, J=2.2 Hz); 4.60(ABq, 1H, J=7 Hz,Δν=12.03 Hz); 5.17(d, 1H, J=2.2 Hz); 7.33–8.27(5H, aromatic protons. Mass (isobutane) m/e (%): 521(50.90); 519(100); 517(50.0).

Diastereomer 3c

I.R. (chloroform cm$^{-1}$: 1815, 1755 (C=O). $^1$H-NMR(300 MHz, CDCl$_3$-TMS)δ(ppm): 1.70 (d, 3H, J=7 Hz); 3.34(d, 1H, J=8.06 Hz); 3.95(s, 3H); 4.05(s, 3H); 4.54(ABq, 1H, J=7 Hz, =11.9 Hz); 4.63(d,1H,J=1.83Hz); 4.68(dd, 1H, J=8.06 Hz, J=1.83 Hz);7.3–8.3(5H aromatic protons).

Diastereomer 3d

M.p.=177° C. I.R. (chloroform) cm$^{-1}$: 1815, 1755 (C=O). $^1$H-NMR(300 MHz. CDCl$_3$-TMS)δ(ppm):1.66(d, 3H, J=7 Hz); 3.40(d,1H J=8.8 Hz); 3.91(s, 3H); 4.05(s, 3H); 4.55(ABq, 1H, J=7 Hz,Δν=12.61 Hz) 4.57(d, 1H, J=1.83 Hz);4.70(dd, 1H, J=8.8 Hz, J=1.83 Hz); 7.3–8.3(5H, aromatic protons). Mass (isobutane) m/e (%): 521(50.61); 519(100); 517(51.4).

All analytical data: I.R. $^1$H—$^{13}$C—NMR (couple, decoupled and selective decoupling), and carbon-carbon connectivity-2D NMR (Bax, A.; Freeman, R. Kempsell, S. P. J.Am.Chem. Soc. (1980 102, 4848, J.Magn.Resonance (1980) 41, 349) are consistent with the structure of compounds 3a, b, c, d.

We claim:

1. A process for preparing alpha-arylalkanoic acids of formula

in which Ar represents 4-isobutyl-phenyl, 3-phenoxy-phenyl, 2-fluoro-4-diphenylyl, 4-(2-thienylcarbonyl)-phenyl, 6-methoxy-2-naphthyl, 5-bromo-6-methoxy-2naphthyl, 6-hydroxy-2-naphthyl, 4-chloro-phenyl or 4-difluoromethoxy-phenyl, and R represents a $C_1$–$C_4$ alkyl or their immediate precursors, comprising heating a compound of formula

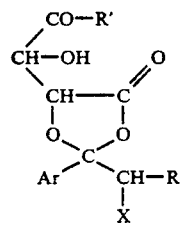

wherein

Ar represents 4isobutyl-phenyl, 3-phenoxy-phenyl, 2-fluoro-4-diphenylyl, 4-(2-thienylcarbonyl)-phenyl, 6-methoxy-2-naphthyl, 5-bromo-6-methoxy-2-naphthyl, 6-hydroxy-2-naphthyl, 4-chloro-phenyl or 4-difluoromethoxy-phenyl;

R represents a $C_1$–$C_4$ alkyl;

R' represents a hydroxyl or an alkoxy $C_1$–$C_4$;

X represents a chlorine, bromine or iodine atom, in a protic polar solvent or in an aprotic dipolar solvent in the presence of a substance having a high dielectric constant, in a neutral or slightly alkaline environment.

2. A process for preparing 2-(6-methoxy-2-naphthyl)-propionic acid or one of its immediate precursors, comprising heating a compound of formula

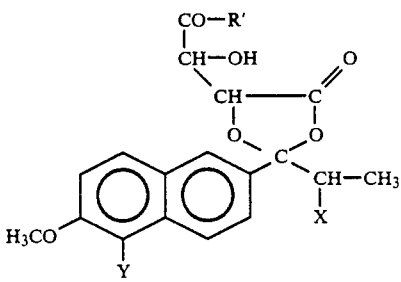

R' represents a hydroxyl or an alkoxy $C_1$–$C_4$;

X represents a chlorine, bromine or iodine atom;

Y represents a hydrogen or bromine atom, in a protic polar solvent or in an aprotic dipolar solvent in the presence of a substance having a high dielectric constant, in a neutral or slightly environment.

* * * * *